United States Patent [19]
Nelson et al.

[11] Patent Number: 5,805,665
[45] Date of Patent: *Sep. 8, 1998

[54] ANTHROPOMORPHIC MAMMOGRAPHY PHANTOMS

[76] Inventors: Robert S. Nelson, 2922 Upshur St., San Diego, Calif. 92106; Reuven D. Zach, 1039 N. Harper Ave., #8, Los Angeles, Calif. 90046

[*] Notice: The term of this patent shall not extend beyond the expiration date of Pat. No. 5,719,916.

[21] Appl. No.: 667,923

[22] Filed: Jun. 12, 1996

Related U.S. Application Data

[63] Continuation-in-part of Ser. No. 470,353, Jun. 5, 1995.
[51] Int. Cl.$^6$ ..................................... G01D 18/00
[52] U.S. Cl. ............................... 378/207; 378/37
[58] Field of Search ....................... 378/37, 207

[56] References Cited

U.S. PATENT DOCUMENTS

| | | |
|---|---|---|
| 3,310,885 | 3/1967 | Alderson . |
| 4,873,707 | 10/1989 | Robertson ................................. 378/18 |
| 5,266,035 | 11/1993 | Olsen et al. . |
| 5,273,435 | 12/1993 | Jacobson . |

OTHER PUBLICATIONS

"A Review of Mammography Test Objects for the Calibration of Resolution, Contrast, and Exposure," by Carolyn Kimme–Smith, Lawrence W. BAssett, and Richard H. Gold Med. Phys. 16(5), Sep./Oct. 1989 pp. 758–765.
Brochure for Mammotest® and MammoVision™ Fischer Imaging Corporation, Denver, Colorado.
Brochure for Anthropomorphic Breast Phantom encased in clear, durable plastic Nuclear Associates, Carle Place, New York.
"Tissue Substitutes in Experimental Radiation Physics," D.R. White Med. Phys. 5(6), Nov./Dec. 1978.
"Phantom for Use in Lung Biopsy Training," WW Scott, JR., JE Kuhlman *Radiology,* (Jul. 1992), pp. 286–287.
"Anderson Radiography Phantoms—The Phantom Patient for Comprehensive Basic Training of Radiologic Technologists" Alderson Research Laboratories, Inc., 8 pgs.
Brochure for "Mammo" . . . The Mammography Training Phantom Nuclear Associates, Carle Place, New York.

*Primary Examiner*—Don Wong
*Attorney, Agent, or Firm*—Lyon & Lyon LLP

[57] ABSTRACT

The present invention provides an apparatus and a method of use and construction of Anthropomorphic Mammography Phantoms. The phantoms resolve deficiencies that currently exist in the practice of mammography x-ray imaging. The mammography phantom provides mammography practitioners a training tool in the practice of proper patient breast positioning and in optimal patient x-ray exposure. The mammography phantom can be used to generate x-ray images similar to mammography patient x-ray images. The mammography phantom simulates normal breast tissue and tissue irregularities and anomalies associated with various known breast pathologies such as microcalcifications, cysts, tumors, etc. The mammography phantom preferably comprises the shape of an upper torso of a woman including one or two breast simulators which can vary in size, density, compressibility, and stretchability. The mammography phantom is preferably constructed such that the breast simulators can be detached from the upper torso phantom, used independently, and/or replaced on the torso thereby enabling the mounting of a variety of breast simulator types. The upper torso of the mammography phantom also preferably provides a rib cage (with pectoralis major muscle) for the mounted breast simulators, providing an additional element of realistic patient simulation.

17 Claims, 5 Drawing Sheets

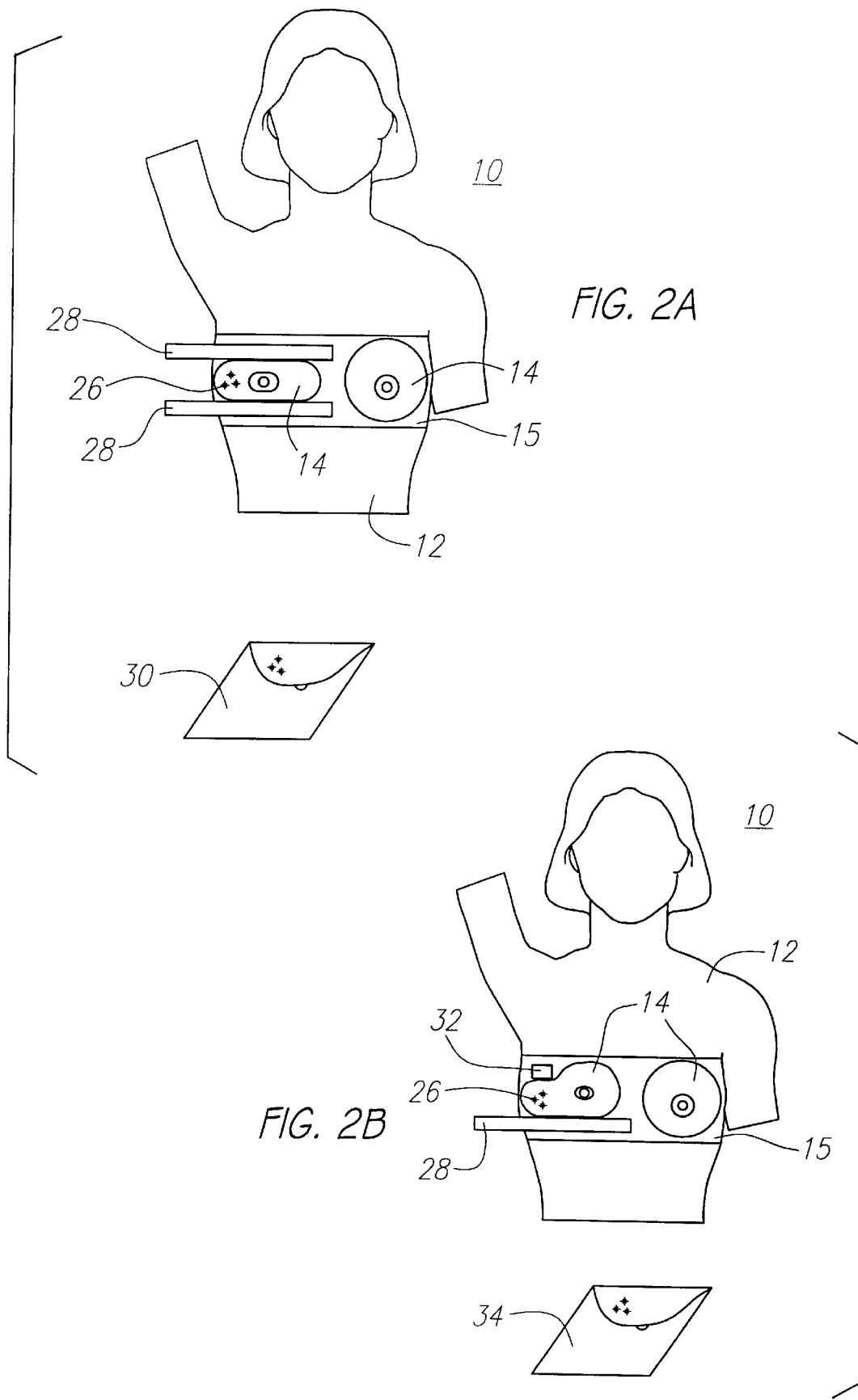

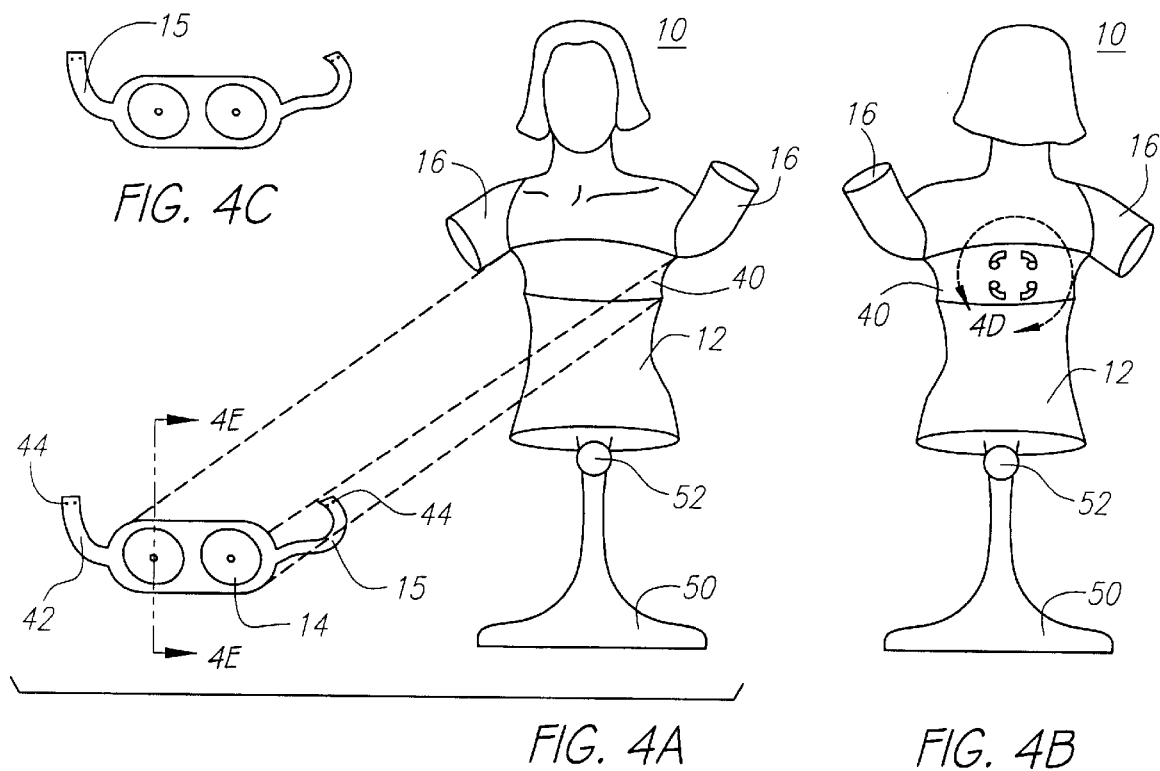
FIG. 4C
FIG. 4A
FIG. 4B
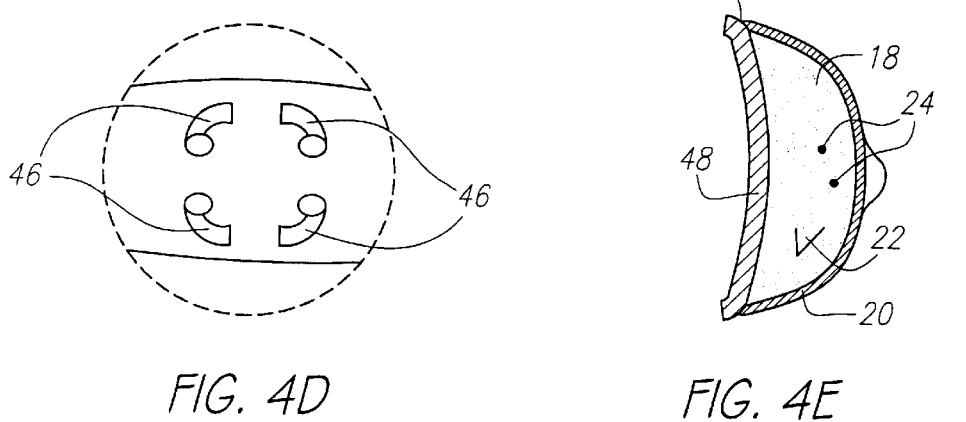
FIG. 4D
FIG. 4E

1

ANTHROPOMORPHIC MAMMOGRAPHY PHANTOMS

RELATED APPLICATION

This application is a continuation-in-part of co-pending application Ser. No. 08/470,353, filed Jun. 5, 1995, the disclosure of which is hereby incorporated by reference as if fully set forth herein.

FIELD OF INVENTION

The present invention relates to phantoms, particularly anthropomorphic mammography phantoms for training and calibration use in mammography applications.

BACKGROUND

Phantoms, in general, play a major role in radiology. Typically, phantoms are used to provide a tool for the assessment and verification of performance standards in daily clinical practice of radiology with respect to the quality of a radiological image and the quantity of an absorbed dose. This is true for general radiology practice, and more so for mammography applications. The purpose of using phantoms in general radiology is to simulate a patient. However, those phantoms intended for general radiology uses are acutely deficient when directed for use in mammography applications. Presently the only phantoms used with mammography are calibration or test phantoms. Not all aspects of mammography x-ray applications are addressed by these phantoms.

While proper calibration of the equipment used in mammography is important (as it is in all x-ray applications), proper breast positioning and proper breast compression are very important as breasts are difficult objects to image and images of breasts are difficult to review. The importance of positioning and compression has been described by those in the industry as being "of paramount importance", "crucial", and "critical" to achieving a usable mammogram.

"Correct patient positioning is of paramount importance in mammography. The breast must be pulled away from the chest wall by the technologist, while compression, vigorous, and, it is hoped, painless, is applied . . . If the technologist is not adept and aggressive in positioning the patient, the mammogram will be inadequate."

Kimme-Smith, et al., *Workbook for Quality Mammography* 2 (1986).

"One-third of the facilities that seek ACR [American College of Radiology] approval do not initially pass muster; in some cases technologists were not adequately trained to position and compress the breast. These skills are crucial because proper compression provides clear, easy-to-interpret views of the breast using the smallest possible dose of radiation. In other centers it's the machines, not the people, that are problematic. Nearly one out of six facilities are initially rejected by the ACR because their equipment is not accurately calibrated."

Harvard Health Letter, Vol. 19 No. 9, Jul. 1994, p. 3. ". . . Experienced radiologists concede that dense breasts are more difficult to image, but believe that good technique enhances mammography's ability to detect cancer in this tissue. . .

. . . 80% of women at age 30 have a dense pattern. The percentage drops to 70% by age 40 and 60% by age 60. By age 60, about half of all women have a fatty pattern and half a dense pattern. . .

The dense breast presents a special technical challenge to mammographers. Because it contains a lot of fibrous tissue, it has less inherent contrast than the fatty breast. Further, cancers often display similar x-ray attenuation to fibrous, glandular [dense] tissue, making them difficult to detect.

Successful imaging of the dense breast begins with taught compression . . . The denser the breast, the more critical adequate compression becomes. Compression helps prevent superimposition of tissue, decreases the amount of scattered radiation, and brings an abnormality closer to the image receptor. The result is a sharper image."

D'Agincourt, *Technique Is Everything When Breast Is Dense*, Diagnostic Imaging 57, 57–58 (Sep. 1993).

Despite recognition of these requirements, phantoms which are currently available for use in mammography do not provide a realistic tool for radiologists to use to train in the proper positioning and/or compressing of breast tissue for mammography purposes.

In addition, the tools currently available for mammography are calibration tools which are designed and limited to the purpose of calibrating the mammography x-ray imaging chain. See, e.g., Kimme-Smith, et al., *A Review of Mammography Test Objects for the Calibration of Resolution, Contrast, and Exposure*, Medical Phys. 758–65 (September/October 1989). Calibration phantoms which are currently available are typically merely blocks of plastic (e.g., acrylic) having tissue equivalent x-ray radiation absorption and/or scattering properties to which may be added grains (e.g., calcium and/or aluminum salts) of varying sizes, e.g., 0.2, 0.5, 0.7, and 1.0 mm. Such phantoms do not have the look or feel of human breasts and do not produce realistic images comparable to patient mammographic images. Therefore, such phantoms do not provide opportunities for developing or improving the positioning skills of mammography technologists, do not provide for developing or improving diagnostic skills of mammogram image interpreters, and do not provide a realistic tool for the calibration of diagnostic mammographic x-ray equipment.

SUMMARY OF THE INVENTION

The present invention comprises anthropomorphic phantoms for use in conjunction with mammography applications. The anthropomorphic phantoms of the present invention address the above described problems and solve other limitations in the current state of the art of ancillary tools employed in mammography applications. The present phantom enhances training and practice of proper patient positioning and patient x-ray exposure. It also can be used to hone a radiologist's ability to detect irregularities in breast tissue by producing phantom mammography images which can simulate many tissue types and tissue irregularities. They further provide better phantoms for use in calibrating mammography x-ray equipment. With the aid of the present phantoms reliability and sensitivity of breast examinations may be improved.

The preferred embodiment of the anthropomorphic mammography phantom of the present invention has the shape of an upper torso of a woman including a phantom breast simulator preferably comprising a pair of simulated breasts (which can be substantially similar to or very different from each other) and which can be varied in size and stiffness (from small to large and from stiff to pendulous), density and firmness, compressibility and stretchiness. The phantom breast simulators are preferably made of materials which mimic the x-ray opacity and physical density of breast tissue or which have x-ray opacity similar to the x-ray opacity of breast tissue. Optionally, density variations representing breast tissue irregularities can be added to the breast simulators. Further, the mammography phantom may include a selective attachment mechanism enabling various breast simulators to be attached to and detached from the phantom torso. Also, the breast simulators may be used as phantoms independent of the phantom torso.

The anthropomorphic breast phantom of the present invention can be used to practice positioning and compression of breasts for mammography purposes, to produce mammographic images similar to mammography x-ray images of patients, and to calibrate x-ray equipment used in mammography. Therefore, with the aid of the present phantom, a technologist can practice realistic positioning and compression of a breast to produce the best mammographic images (as described above and in other references); radiologists can hone their diagnostic skills in reviewing and interpreting breast radiographic mammographic images; and mammography equipment can be calibrated.

It is, therefore, a primary object of the present invention to provide an improved anthropomorphic phantom which substantially mimics the x-ray radiographic imaging properties of human female breasts.

It is an additional object of the present invention to provide an anthropomorphic phantom to use in mammography applications.

It is a further object of the present invention to provide an anthropomorphic phantom which enhances training and practice of proper mammographic patient positioning.

It is another object of the present invention to provide an anthropomorphic phantom which enhances training and practice of proper patient mammography x-ray exposure.

It is also an object of the present invention to provide an anthropomorphic mammography phantom which can be used to teach, test, and/or improve radiologists' ability to detect breast tissue irregularities.

It is yet a further object of the present invention to provide a phantom for use in calibrating mammography x-ray equipment.

Other objects and features of the present invention will become apparent from consideration of the following description taken in conjunction with the accompanying drawings.

BRIEF DESCRIPTION OF THE DRAWINGS

FIG. 2A is a front view of a breast phantom showing a breast simulator subjected to standard mammography compression and an x-ray image which may result from the same and which shows unresolved overlap of tissue abnormalities in the breast simulator.

FIG. 2B is a front view of a breast phantom showing a breast simulator subjected to spot compression and an x-ray image which may result from the same and which shows resolved images of the tissue abnormalities in the breast simulator due to the compression.

FIG. 4A is a front perspective view of a breast phantom of the present invention.

FIG. 4B is a back perspective view of a breast phantom of the present invention.

FIG. 4C is a perspective view of a removable unit comprising two breast simulators of the present invention.

FIG. 4D is an enlarged view of the breast simulator unit attachment mechanism shown in FIG. 4B.

FIG. 4E is a cross-sectional view of a breast simulator taken along line 4E—4E in FIG. 4C.

DETAILED DESCRIPTION OF THE PREFERRED EMBODIMENT

Figure 1A:
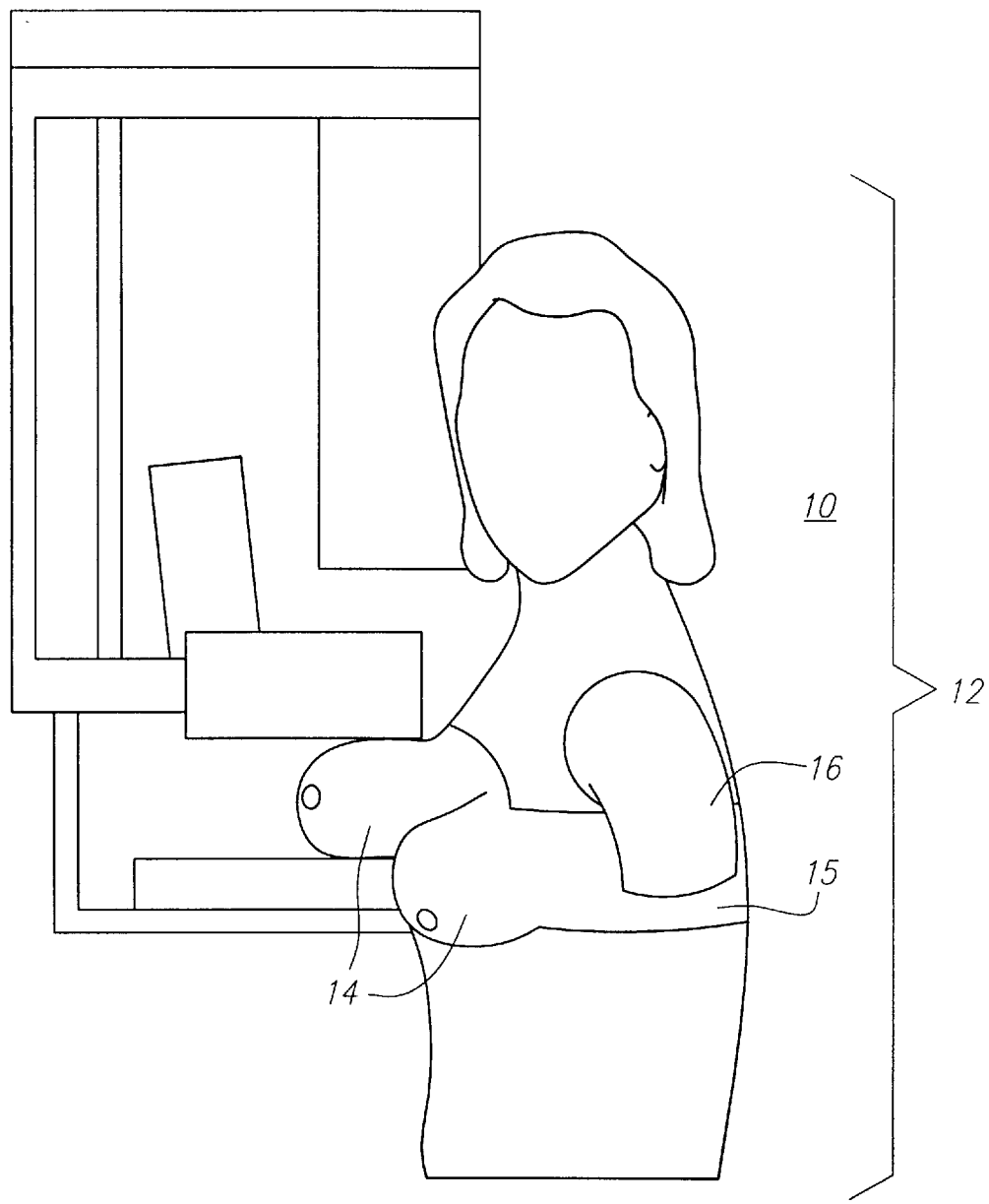
FIG. 1A is a perspective view of a preferred embodiment of the present mammography phantom with a detachable breast simulator positioned for x-ray examination.
Figure 1B:
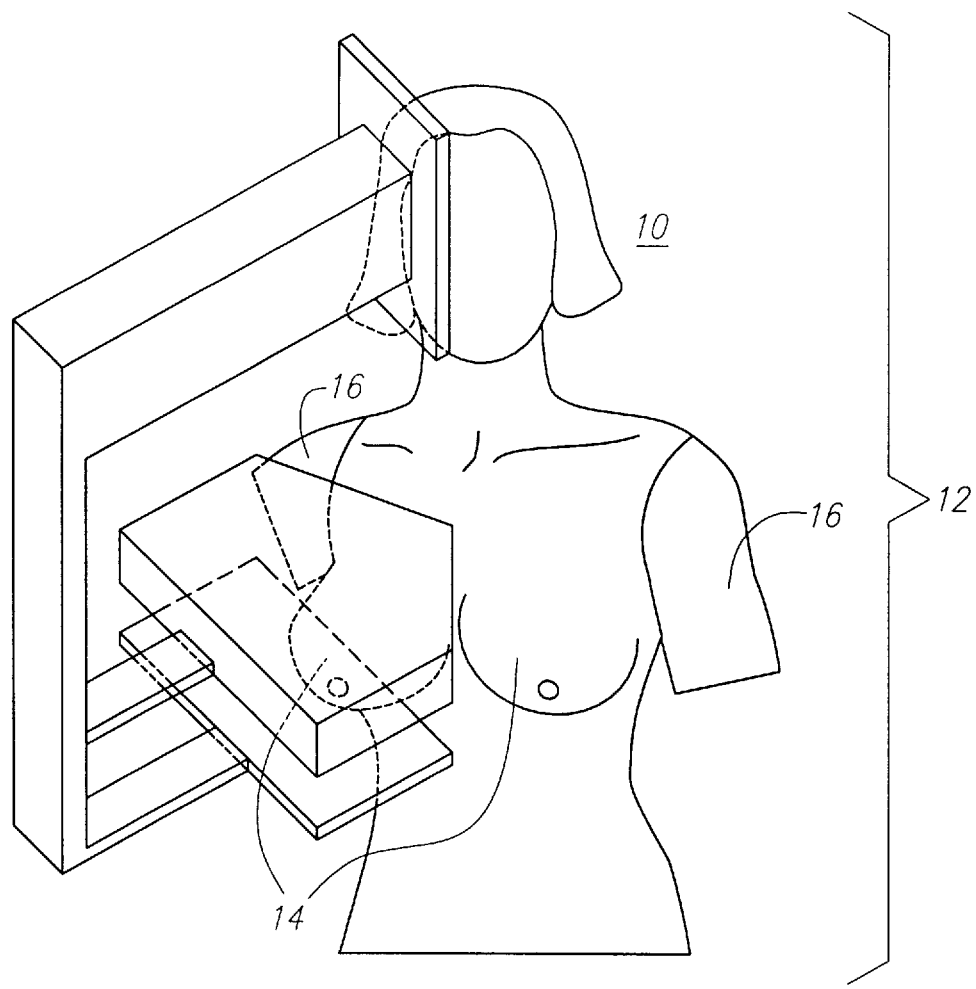
FIG. 1B is a perspective view of a second embodiment of the anthropomorphic mammography phantom of the present invention with a breast simulator positioned for x-ray examination.

Turning now to the drawings in detail, FIGS. 1A, 1B, and 4A show alternative embodiments of the anthropomorphic mammography phantom 10 of the present invention. As is shown in FIGS. 1A and 1B, the phantom 10 preferably substantially simulates a human female upper torso and more particularly, comprises an upper torso 12 which includes a pair of breast simulators 14 and which can include adjustable arms 16 (to help mimic patient movement of stretching chest and breast ligaments). The pair of breast simulators 14 preferably comprises a detachable unit 15 as is shown in FIGS. 1A, 4A, and 4C, and may be used as a phantom independent from the torso 12. Although the preferred embodiment includes a pair of breast simulators 14 a phantom can have one or more breast simulators.

Figure 1C:
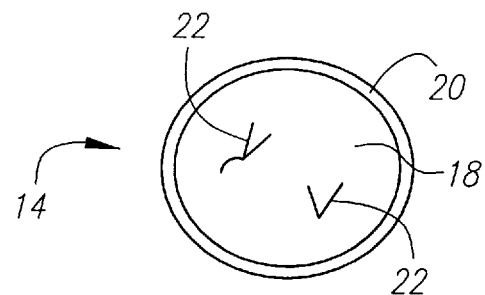
FIG. 1C is a cross-sectional view of a breast simulator of the present invention.

As is shown in FIGS. 1C and 4E, each breast simulator 14 comprises one or more suitable core materials 18 (such as powdered, liquid, gel, and solid materials), encased by a textured skin-like cover 20. For example, a suitable core material is a dry powder enclosed with a desired amount of dry gas, such as dry flour, talc, powdered sugar, corn starch, dried milk, fine flaked or powdered cereals, fine plastic spheres, fine spheres of other suitable materials, etc., combined with dry air, etc., and encased in a cover 20. Another acceptable example of suitable material is a liquid, such as oil (e.g., synthetic, animal, organic (soy, safflower, peanut, corn, olive, rapeseed, palm, etc.)) encased by a textured skin-like cover 20. The liquid may be soaked in a foam or sponge material which is then encased by the cover 20. Yet another example of suitable material is a solid such as fat (e.g., butter fat), gel, gelatin, cured, soft rubber, gum rubber, etc., plastic foam, sponge, foam soaked in gel, etc., encased by a textured skin-like cover 20.

The core materials 18 can be spiked with chemical additives to adjust their x-ray attenuation properties if desired. For example, materials having greater x-ray opacity may be added to the original core materials 18 to increase the x-ray opacity of the simulator 14.

Different core materials 18 have different advantages and disadvantages. For example, solids and powdered materials can better tolerate punctures in the skin-like cover 20; powders and liquids can more easily and cheaply be removed and replaced; solids and gels may be permanently attached to skin-like cover 20 and not allow removal or replacement; powders, liquids and gels can be more easily and evenly spiked to adjust x-ray opacity; air content of powders can more easily be changed to alter x-ray opacity; powders and liquids require the skin-like cover 20 to provide elastic forces to restore the simulator 14 to an original shape and/or size; a solid sponge or foam like material soaked in liquid can provide an elastic shape/form restoring source; gel materials can also provide elastic forces; materials with elastic forces may allow reduction in thickness of skin-like cover 20 or may allow a different material to be used for the skin-like cover 20. A solid core material (including gels) could permit embedded structures to be fixed (immobilized) in position without the use of internal baffles or wires as support.

The simulator 14 preferably also contains additional structures 22 embedded in or attached to the core materials 18. Each breast simulator 14, including core material 18 and skin-like cover 20, simulates mechanical (compressibility, elasticity, etc.) and x-ray radiological properties of a human breast, however, they need not be substantially identical to each other.

A preferred embodiment of the breast simulators 14 of the present invention preferably comprise the following materials: The core material 18 is preferably dry powder mixed with desired chemicals to adjust the x-ray opacity of the powder and dry gas encased by a skin-like cover 20. Suitable materials are baking flour, with added baking powder and salt, such as "self rising, enriched, bleached and presifted" bread flour and dry air which are readily available. The skin-like cover 20 preferably comprises latex, a latex-like silicon cover, or a room temperature vulcanized silicon-rubber, which are readily available. It is preferable that the skin-like cover 20 encase the core material 18 and substantially prevent enclosed gas from escaping. The skin-like cover 20 may be any color or may be transparent. It is preferred that the cover 20 be skin-colored, and that the inside contents of the simulator 14 not be visible therethrough. However, certain applications may benefit from the cover 20 being transparent and the contents of the simulator 14 being visible therethrough (e.g., mammography stereotactic calibration and training).

In an additional embodiment the breast simulator 14 of the present invention includes a small vent or valve to enable the introduction of gas (e.g., dry air, etc.) to replace any gas which escapes from the simulator. Such a vent is well known in the art. The gas may escape at a non-detectable rate over a period of time and, eventually, it is preferred that the simulator be, in a sense, reinflated. It is preferred that such a vent or valve be located at a position so as to not interfere with the breast-like look or feel of the simulator 14. Therefore, it is preferred that the vent or valve be positioned through the side opposite where a simulated nipple of the breast simulator 14 would expectedly be positioned.

The physical dimensions of the breast simulator 14 of the present invention may vary widely. However, the breast simulator 14 preferably has physical dimensions similar to those of a human female breast. The mass of core material 18 may also vary, and is preferably sufficient to simulate the mass of a human female breast. With respect to a preferred embodiment the core material 18 is a dry powdered material and further includes dry gas to enable the powder to move inside the simulator 14 even when the simulator 14 is compressed or otherwise manipulated. For example, an acceptable physical state may be achieved by filling a piece of latex with approximately 500 grams of dry baking flour and sealing the same so the size of the filled latex is approximately 10 cm in diameter and approximately 12 cm in axial length, then injecting approximately 10–50 cc of dry air into the latex to achieve a preferred look and/or feel.

The embedded structures 22 are preferably x-ray absorbent materials such as grains of metal (e.g., sodium, calcium, or aluminum salt grains) or finely crushed egg shells which can be inserted into the powder or glued to the inner surface of the skin-like cover 20 of the simulator. Such metal salts and egg shells are readily available. Additional embedded materials can include a metallic fine wool such as aluminum or steel or copper wool which can be layered between the interior material 18 and latex exterior 20 or which can be integral to the interior material 18. Further embedded materials include a non-metallic fibrous materials such as plastic wool which may be coated with another non-metallic material such as wax and which may be layered between the interior material 18 and skin-like cover 20 or which may be integral to the interior material 18. Additional embedded materials are bead-like objects made of materials such as wax, plastic, or sealed liquids or gels having image contrast which is dependent on the x-ray tube voltage (KVp).

As is described above, a preferred interior material 18 is preferably x-ray absorbent and preferably a powder and gas combination. It is preferred that the powder for the present invention be x-ray absorbent and include x-ray absorbent materials such as liquids or gels sealed in plastic (e.g., small plastic bags) and/or metallic material(s) either substantially homogeneously distributed throughout the core 18 or layered on the surface of the core 18 or inner surface of the cover 20. Such material can be provided, for example, via a structural component (e.g., fine mesh or wool-like material) layered on or embedded in the powder and coated with paint containing x-ray absorbing metals which produce the desired x-ray opacity. The only requirement is that the x-ray absorbing substance be located in the pathway of the x-rays when the simulator is imaged thereby causing the simulator to have the desired level of x-ray opacity and produce the desired x-ray mammography image.

As is shown in FIG. 1B, in one embodiment of the phantom 10 the breast simulators 14 are permanently fixed to the upper torso 12. As is shown in FIGS. 1A, 4A, and 4C, and described above, in a second embodiment of the phantom 10 the breast simulators 14 comprise a breast simulator unit 15 which is detachable from the upper torso 12 of the phantom 10. Having the breast simulators 14 as a detachable unit 15 enables mounting different breast simulators 14 to a single phantom 10 torso 12 and/or the use of the breast simulators 14 independent from the torso 12.

For example, breast simulator units 15 can be manufactured to include breast simulators 14 which mimic breast types varying in size, shape and internal construction. Breast simulators 14 can also be manufactured to simulate breast characteristics found in x-ray mammographic images, such as fibrils, lesions, dense regions, microcalcifications, and masses with calcification; as well as arteries and veins, adipose and glandular tissue etc. Breast simulators 14 can be constructed to simulate any desired tissue abnormality which can be imaged with x-ray mammography. Breast simulators 14 can also be constructed to simulate abnormalities of breast duct structures which are usually imaged through contrast enhanced mammography.

While other methods of attaching the breast simulators 14 (either individually or as a unit 15) to the torso 12 are acceptable, as is shown in FIGS. 4A and 4B, the torso 12 of the phantom 10 preferably includes a channel or indented area 40 into which the breast simulator unit 15 can be securely aligned. The breast simulator unit 15 can be securely tied around the torso 12 or, as is shown in FIGS. 4B, 4C, and 4D, the breast simulator unit 15 can be attached to the phantom 10 by an aperture and pin arrangement.

Specifically, FIG. 4C shows that the breast simulator unit 15 preferably comprises a belt-like structure 42 to which the breast simulators 14 are attached. The belt structure 42 can have stretchable portions and, as is shown in FIG. 4C, preferably includes apertures 44. Furthermore, FIGS. 4B and 4D show that the back of the phantom 10 preferably includes pins 46 which correspond to the apertures 44 in the belt structure 42. To attach the breast simulator unit 15 to the torso 12 of the phantom 10 the belt 42 preferably is aligned with the channel 40 of the torso 12 and stretched around the torso 12 to hook the apertures 44 onto the pins 46. The combination of the channel 40 and the aperture/pin 44/46 arrangement allows the unit 15 to be tightly attached to the torso 12 such that the breast simulators 14 can be manipulated without substantially disturbing the positioning of the simulators 14 with respect to the torso 12.

The upper torso 12 of the phantom 10 also serves as a rib cage simulator (with simulated pectoralis major muscle) in addition to providing a mounting surface for the breast simulators 14 thereby providing an additional element of realistic patient simulation. The rib cage simulator and simulated pectoralis major muscle preferably comprise plastic material which is readily available and preferably are components of the torso portion 12 of the present phantom 10. In addition, as is shown in FIG. 4E, the breast simulator unit 15 includes a chest wall portion 48 which simulates a patient's chest wall and is useful in training technicians on the proper positioning of a patient as is described in greater detail below. As is also shown in FIG. 4E, the chest wall portion 48 is preferably at least slightly convex. In addition, it is preferred that the breast simulator unit 15 simulates any portion of the torso 10 which is "missing" due to inclusion of the indented area 40. For example, a portion of the simulated rib cage (and pectoralis major muscle) of the torso 10 might be removed to incorporate the indented area 10 into the phantom 10 and, in such a case, the breast simulator unit 15 preferably includes that missing portion. Therefore, when the breast simulator unit 15 is mounted to the torso 10 (in the indented area 40) the full rib cage is simulated providing a realistic look and feel.

The anthropomorphic mammography phantom 10 of the present invention can be used for calibrating a mammography unit by imbedding in the breast simulators 14 structures 24, as shown in FIG. 4E, whose imaged contrast depends on the applied x-ray tube voltage (kVp). Such structures or a distinct subset of these structures detected in a mammographic image can be used to indicate that the proper kVp and optimal x-ray exposure were used. Importantly, such structures help to test and train technologists in the proper placement and positioning of patients undergoing mammography.

One example of structures 24 whose imaged contrast depends on the applied kVp are bead-like objects made of materials such as wax, plastic, or sealed liquids, or sealed gels having image contrast which is kVp dependent. Detection of the images of these imbedded structures allows assessment of the applied kVp settings. In addition, these bead-like objects may be used to simulate cysts present in patient breast tissue.

Materials which include wool-like metal and non-metal fibrous materials (such as steel wool, aluminum wool, copper wool, cotton wool coated or soaked with special chemicals, plastic thread, coated plastic threads, silicon-plastic fibers, spiked plastic fibers, etc.) can be distributed inside a breast simulator to produce mammographic images closely resembling patient x-ray mammography breast images depicting characteristic glandular and/or dense tissue. In addition, materials having a desired x-ray opacity such as metal salt grains or grains of crushed egg shells preferably ranging in size from approximately 0.1 mm to approximately 2.0 mm in diameter can be imbedded inside a breast simulator 14 to produce mammographic images with features closely resembling patient breast images which include microcalcifications. The imbedded grains can be grouped into distinct patterns. In one embodiment, grains can be grouped in such a way so that their images overlap images of other grains and/or images of wool-like materials (described above) simulating dense tissue with microcalcifications. The grouping and/or overlap of such structures simulates the appearance of microcalcifications inside patient dense tissue.

In another embodiment, grains can be grouped to facilitate assessment of image resolution. The grain groupings need not be spaced or patterned in any particular or reproducible manner. The grains can be manufactured into the breast simulators 14 or they can be injected (e.g., using a needle and syringe) into a breast simulator 14 at a later time.

In yet another embodiment, fine metallic mesh strip(s) can be imbedded inside the breast simulator 14. The image of the mesh facilitates image resolution assessment. Mammography images of breast simulators which include thin, sub-millimeter metal wool, for instance, also aid in the assessment of system resolution. Contrast and resolution features found in existing devices and test phantoms that are required for compliance with the Mammography Quality Standards Act can be incorporated into the anthropomorphic mammography phantom of the present invention thereby enabling the anthropomorphic mammography phantom to also be utilized as a mammography calibration tool.

One implementation of the anthropomorphic mammography phantom 10 of the present invention simulates patient motion (such as breathing, heart beating, and blood flowing) by pulsing the phantom and thereby permitting x-ray technologists to assess the effect of patient motion on image quality. The phantom can include tubing attachable to a simple pump which is used to pulse liquid or gas through the tubing to simulate patient motion. Yet another implementation of the anthropomorphic mammography phantom 10 simulates the effect of the heart pumping blood or blood with x-ray contrast dyes by embedding hollow tubes into the breast simulators 14 of the phantom 10. A pump is used to pulse and/or circulate the appropriate liquids. Realistic angiographic conditions are simulated by injecting an x-ray contrast dye into the circulating liquid.

The phantom 10 of the present invention can be mounted on a portable stand with adjustable height and inclination to aid in breast/phantom positioning. For example, as is shown in FIGS. 4A and 4B, the phantom 10 can be attached to a base 50 via a swivel support 52 which allows the phantom 10 to be tilted (preferably, e.g., 20–30 degrees) and allows the phantom 10 to be rotated.

Breast simulators 14 including imbedded material having image overlap can be used for training proper breast positioning and proper breast compression. As is shown in FIGS. 2A and 2B, proper breast compression resolves overlapping images. FIG. 2A shows a front view of a breast simulator 14 including underlying structures 26 being compressed using standard compression by two compression plates 28 and shows a resulting image 30. As is shown, the resulting image 30 includes overlap from the images of the underlying structures thereby producing a shadow which would typically be flagged as an abnormality by a radiologist interpreting the results. As is described below, proper compression would separate overlapping structures thereby providing improved diagnosis of the tissue (i.e. by resolving the images of the structures).

FIG. 2B shows a front view of the same breast simulator 14 and underlying structures 26 as in FIG. 2A and shows the resulting image 34. However, FIG. 2B shows the breast simulator 14 and structures 26 being compressed using spot compression between a lower compression plate 28 and a spot compressor 32. As is shown, the resulting spot-compression image 34 spreads out the x-ray images of the structures 26 thereby allowing proper interpretation of the image and subsequent diagnosis.

Figure 3A:
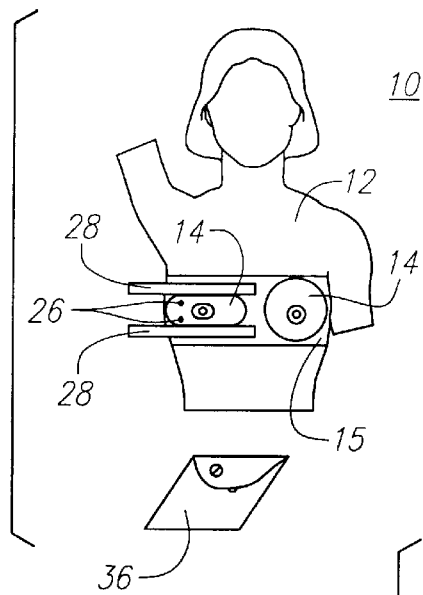
FIG. 3A is a front view of a breast phantom showing a breast simulator subjected to standard compression and an x-ray image showing unresolved overlap of tissue abnormalities in the breast simulator.
Figure 3B:
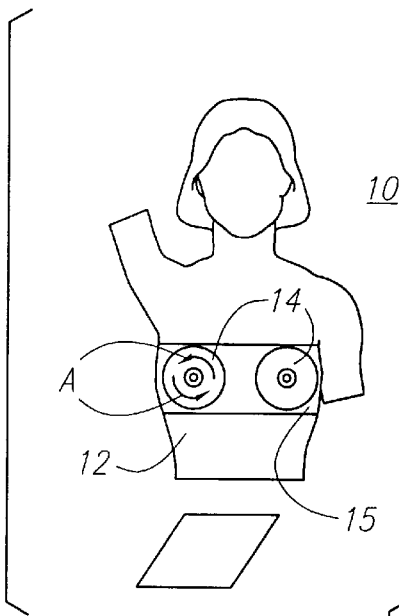
FIG. 3B is a front view of a breast phantom showing the breast simulator from FIG. 3A being rotated.
Figure 3C:
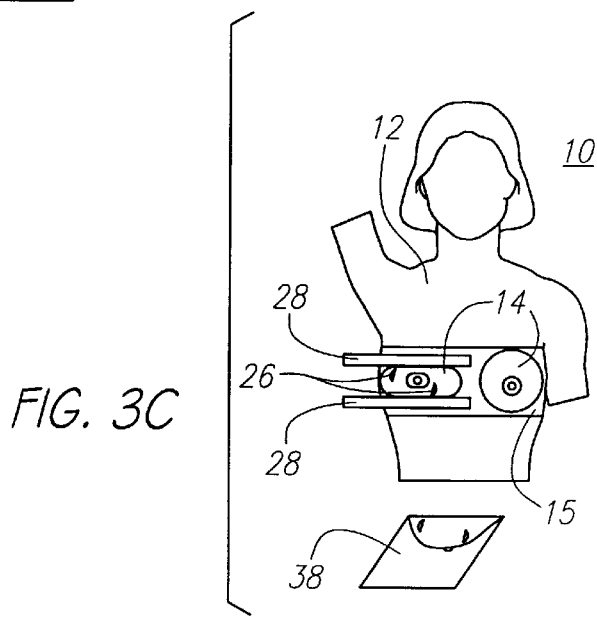
FIG. 3C is a front view of a breast phantom showing the rotated breast simulator from FIG. 3B subjected to standard compression and an x-ray image showing resolution and separation of the tissue abnormalities from FIG. 3A due to the rotation.

As is shown in FIGS. 3A and 3C, proper breast positioning also resolves overlapping images. FIG. 3A shows a front view of a breast simulator 14 including underlying structures 26 being held in a standard position by two compression plates 28 and shows a resulting image 36. As is shown, the resulting image 36 includes overlap from the images of the underlying structures 26 thereby producing a shadow which would typically be flagged as an abnormality by a radiologist interpreting the results. Proper breast re-positioning resolves the images thereby resolving the apparent abnormality. FIG. 3B shows repositioning the breast simulator 14 by rotating the top of the breast medially and the bottom of the breast laterally (as indicated by the arrows A in FIG. 3B).

FIG. 3C shows a front view of the breast simulator 14 and underlying structures 26 from FIG. 3A and shows the resulting image 38. However, FIG. 3C shows the breast simulator 14 and structures 26 after the breast simulator 14 was rotated as described above. As is shown, the resulting repositioned image 34 spreads out the images of the structures 26 thereby allowing proper interpretation of the image and subsequent analysis.

Both spot compression and breast rotation are techniques which are used to improve mammographic images. The anthropomorphic mammography phantom 10 of the present invention provides x-ray technologists an opportunity to realistically practice the compression and positioning techniques such as described above which currently available phantoms do not.

While embodiments of the present invention have been shown and described, various modifications may be made without departing from the scope of the present invention, and all such modifications and equivalents are intended to be covered.

What is claimed is:

1. An apparatus for mammography training and mammographic system calibration, said apparatus having anthropomorphic features and comprising at least one breast simulator comprising a material having human breast-like mechanical and x-ray radiographic imaging properties making the simulator suitable for at least one of mammography training and mammographic system calibration, wherein the breast simulator has a core comprising at least one of powdered, liquid, and solid material and a cover.

2. The apparatus of claim 1 wherein the core comprises powdered material comprising at least one of flour, talc, powdered sugar, cornstarch, dried milk, powdered cereals, flaked cereals, and plastic spheres.

3. The apparatus of claim 1 wherein the core comprises liquid material comprising at least one of synthetic oil, organic oil, and oils derived from animals.

4. The apparatus of claim 1 wherein the core comprises solid material wherein the solid material comprises at least one of gel, gelatin, fat, butter fat, foam, sponge, rubber, gum rubber, and wool-like material.

5. The apparatus of claim 4 wherein the wool-like material is at least one from the group consisting of steel wool, aluminum wool, copper wool, treated cotton wool, plastic wool, and silicon-plastic fibers.

6. The apparatus of claim 1 wherein the at least one breast simulator is attachable to a human-like upper torso structure.

7. The apparatus of claim 1 comprising at least two breast simulators wherein the breast simulators comprise one or more shape, size, mammographic x-ray opacity, composition, stiffness, pendulousity, hardness, elasticity, compressibility, resiliency, and restitution.

8. The apparatus of claim 1 comprising at least two breast simulators wherein the simulators comprise one or more shape, size, mammographic x-ray opacity, composition, stiffness, pendulousity, hardness, elasticity, compressibility, resiliency, and restitution, and simulate one or more regular breast tissue, irregular breast tissue, a breast implant, and a breast with contrast enhancing dye under x-ray exposure.

9. The apparatus of claim 1 further comprising at least one object having a desired x-ray opacity embedded in the breast simulator and comprising one or more size, shape, mammographic x-ray opacity, and radiological x-ray contrast.

10. The apparatus of claim 9 wherein the at least one object imbedded in the breast simulator comprises one or more grains.

11. The apparatus of claim 9 wherein the at least one object imbedded in the breast simulator comprises a piece of fine metallic mesh.

12. The apparatus of claim 9 wherein the at least one object imbedded in the breast simulator comprises a material having an image contrast which is dependent on x-ray tube voltage used to image it.

13. The apparatus of claim 1 wherein the cover comprises latex.

14. The apparatus of claim 1 wherein the cover comprises silicon rubber.

15. The apparatus of claim 1 wherein the cover is transparent.

16. The apparatus of claim 1 wherein the cover is colored.

17. the apparatus of claim 1 wherein the breast simulator further comprises a valve enabling the passage of gas through the cover.

* * * * *